United States Patent [19]

Vince

[11] 4,268,672
[45] May 19, 1981

[54] ADENOSINE DEAMINASE RESISTANT ANTIVIRAL PURINE NUCLEOSIDES AND METHOD OF PREPARATION

[75] Inventor: Robert Vince, St. Paul, Minn.

[73] Assignee: The Regents of the University of Minnesota, Minneapolis, Minn.

[21] Appl. No.: 1,072

[22] Filed: Jan. 5, 1979

Related U.S. Application Data

[63] Continuation-in-part of Ser. No. 766,947, Feb. 9, 1977, Pat. No. 4,138,562.

[51] Int. Cl.³ .............................................. C07D 473/34
[52] U.S. Cl. .................................................. 544/265
[58] Field of Search ....................... 544/264, 265, 277

[56] References Cited

PUBLICATIONS

L. Bennett et al., Mol. Pharmacol. 4, 208–217 (1968), Metabolic Studies with Carbocyclic Analogs of Purine Nucleosides.
D. Hill et al., Chem. Abstracts, 75:86554s (1971), Inhibition of Guanine Metabolism of Mammalian Tumor Cells by the Carbocyclic Analog of Adenosine.
Y. Shealy et al., 4 Amer. Chem. Soc., (1969), 91, (11), 3075–3083, Synthesis of Carbocyclic Analogs of Purine Ribonucleosides.
A. Holy, Nucleic Acids Research, Spec. Publ., 1975, 1 (Symp. Chem. Nucleic Acids Components, 3rd, 1975), 573–576.

Primary Examiner—Glennon H. Hollrah
Assistant Examiner—M. C. Eakin
Attorney, Agent, or Firm—Burd, Bartz & Gutenkauf

[57] ABSTRACT

The preparation of (±)-9-[α-(2α,3β-dihydroxy-4α-(hydroxymethyl)cyclopentyl)]-6-substituted purines:

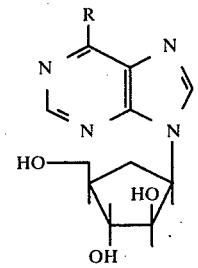

and (±)-3-[α-(2α,3β-dihydroxy-4α-(hydroxymethyl)cyclopentyl)]-7-substituted-v-triazolo[4,5d]pyrimidines:

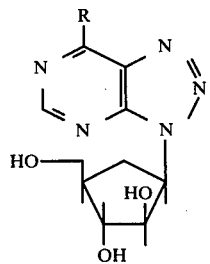

and their derivatives wherein R is amino, mercapto, methylmercapto, hydroxy, halogen, or substituted amino:

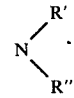

wherein R' and R" may be the same or different and are of hydrogen, methyl, ethyl, propyl or phenyl. The preparation of the single intermediate from which either of these series of compounds may be synthesized is also disclosed. The compounds exhibit antiviral and antitumor activity. Acid salts and esters of the purine nucleosides have also been prepared.

5 Claims, 1 Drawing Figure

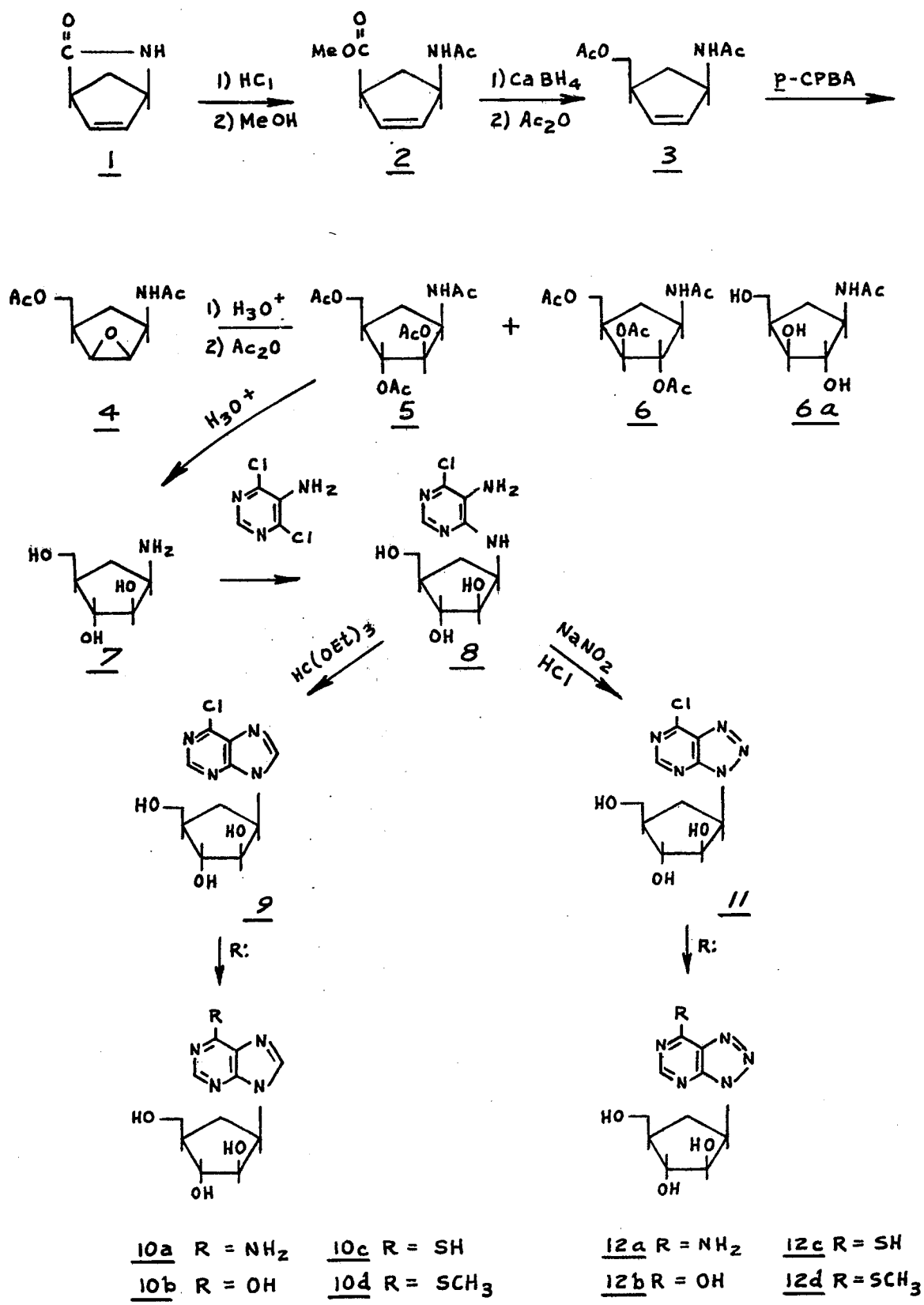

ADENOSINE DEAMINASE RESISTANT ANTIVIRAL PURINE NUCLEOSIDES AND METHOD OF PREPARATION

The invention described herein was made in part in the course of work under a grant or award from the Department of Health, Education and Welfare.

This application is a continuation-in-part of my copending application Ser. No. 766,947, filed Feb. 9, 1977, now U.S. Pat. No. 4,138,562, issued Feb. 6, 1979.

BACKGROUND OF THE INVENTION

1. Field of the Invention

The invention is directed to the preparation of certain chemotherapeutic materials useful in the treatment of viral infections and tumors associated with viruses. More specifically, the invention is directed to the preparation of adenosine deaminase resistant antiviral purine nucleosides.

2. Description of the Prior Art

The antiviral nucleoside 9-β-D-arabinofuranosyladenine (ara-A) was first synthesized in a program designed to produce anticancer agents. Recent interest in the promising antiviral activity of ara-A has been extensively reviewed. Broad spectrum activity of ara-A against DNA viruses and significant therapeutic activity of ara-A against experimental herpes simplex keratitis and herpes simplex and vaccinial encephalitis has been reported. A major liability in the use of ara-A lies in the fact that the nucleoside is rapidly deaminated by a commonly occurring enzyme, adenosine deaminase. Deamination of ara-A renders it much less effective and high doses of the drug are required at frequent intervals. Although the deamination product, 9-β-D-arabinofuranosyl-hypoxanthine (ara-H), is also active against DNA viruses, it is considerably less active than ara-A. A major effort to circumvent the deamination problem employs the use of ara-A in combination with adenosine deaminase inhibitors such as deoxycoformycin or erythro-9-(2-hydroxy-3-nonyl)adenine. This approach presents a problem in that the Food and Drug Administration is reluctant to approve and physicians are reluctant to prescribe a compound that inhibits an enzyme with a normal body function. A more desirable approach to the development of a more active antiviral or antitumor agent, followed by applicant, involves the use of a deamination resistant ara-A derivative. The carbocyclic ara-A analogs described herein circumvent the major disadvantage of ara-A because they are completely resistant to degradation by adenosine deaminase.

SUMMARY OF THE INVENTION

The invention is directed to the synthesis of the intermediate:

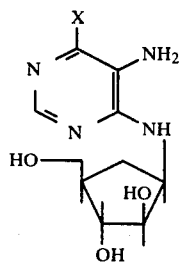

wherein X is a halogen, and the synthesis from it of either of the purine nucleosides:

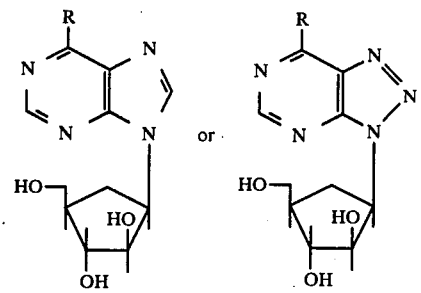

wherein R is amino, hydroxyl, mercapto, methylmercapto or substituted amino:

wherein R' and R" are either the same or different and are hydrogen, methyl, ethyl, propyl or phenyl.

BRIEF DESCRIPTION OF THE DRAWING

The single FIGURE of the accompanying drawing is a flow diagram showing the synthesis of the purine nucleosides.

DESCRIPTION OF THE PREFERRED EMBODIMENTS

The recent description of an unequivocal route to 2-azabicyclo[2.2.1]hept-5-en-3-one (1, referring to the corresponding number on the flow sheet) (Jagt et al., J. Org. Chem., 39, 564 (1974)) offers a unique starting point for the synthesis of carbocyclic aminonucleosides of known geometric configuration. Acidic hydrolysis of this compound to cis-4-aminocyclopent-2-ene carboxylic acid hydrochloride, followed by esterification of the carboxyl function in refluxing methanol and subsequent acetylation of the amino group in acetic anhydride-pyridine, gives methyl (±)-cis-4-acetamidocyclopent-2-ene carboxylate (2). Reduction of the methyl ester of 2 gives, after acetylation, acetate 3. Epoxidation of acetate 3 is stereoselective due to the syn-directing allylic amide group, giving only the cis-epoxide 4. Hydrolysis of the easily synthesized epoxide 4 and subsequent acetylation gives a mixture of 5, 6 and 6a.

When the major isomer, (±)-4α-acetamido-2β,3α-diacetoxy-1α-cyclopentanemethyl acetate (5) is subjected to mild acidic hydrolysis, amine 7 is formed, since acyl migration to the adjacent cis-hydroxyl facilitates hydrolysis of the acetamide. Amine 7, a hygroscopic gum, is immediately condensed with 5-amino-4,6-dihalopyrimidine, giving intermediate 5-amino-4N-[2α,3β-dihydroxy-4α-(hydroxymethyl)cyclopent-1α-yl]amino-6-halopyrimidine (8). This intermediate, when treated with the ring closing reagents leads to the preparation of two series of purine nucleoside analogs, 9 and 11.

The nucleoside analogs (called carbocyclic arabinosyl adenosine analogs) 9 and 11 can be converted to a series of antiviral and antitumor agents by reaction with substituting agents for adding a substituent in the 6-position of 10 or the 7-position of 12. These substituting agents (R:) are selected from the group consisting of amino, mercapto, methylmercapto, hydroxy and substituted amine. The antiviral compounds are represented by structures 10 and 12.

The invention is illustrated by the following examples:

EXAMPLE 1

The intermediate, 5-amino-4N-[2α,3β-dihydroxy-4α-(hydroxymethyl)cyclopent-1α-yl]amino-6-chloropyrimidine (8), was prepared as follows:

Methyl (±)-cis-4-acetamidocyclopent-2-enecarboxylate (2). 2-Azabicyclo[2.2.1]heptan-3-one (Jagt et al., J. Org. Chem., 39, 564 (1974)) (64.2 g., 0.588 mole) was dissolved in 5% HCl (2500 ml) and the solution stirred at room temperature (RT) for 3.5 days. A small amount of gummy solid was filtered off, and the filtrate was cooled (ice bath) while sufficient 6 N NaOH (ca. 500 ml) was added to give pH 1.0. The pale yellow solution was evaporated to dryness (<50°, 0.5 mm). The residue was azeotroped with PhH—MeOH, dried at 0.1 mm/RT, and then refluxed in dry MeOH (1 liter) for 18 hrs. The NaCl was filtered off and washed with additional MeOH. The MeOH filtrate-wash was evaporated to dryness and the residual yellow syrup dissolved in pyridine (500 ml). Acetic anhydride (300 ml) was added to the cooled (ice bath) solution. The solution was allowed to come to RT. After 1.0 hr. at RT, the solution was evaporated (<50°, 0.5 mm) to dryness. The residue was dissolved in $CH_2Cl_2$ (500 ml) and extracted with sat'd $NaHCO_3$ (3×200 ml), sat'd NaCl (50 ml), and dried ($CaSO_4$). Evaporation and azeotroping with toluene (3×200 ml, to remove pyridine) left a yellow syrup (103.5 g) which solidified within a few minutes with the generation of considerable heat. The nmr spectrum of this off-white solid was identical with that of an analytical sample. Sublimation (70°–80°, 0.003 mm) gave methyl-cis-4-acetamidocyclopent-2-enecarboxylate as white crystals (96.1 g, 89%); mp 66°-67° (±)-cis-4-Acetamidocyclopent-2-enemethyl Acetate (3). A mixture of $CaCl_2$ (31.8 g, 0.286 mole) and $NaBH_4$ (21.7 g, 0.572 mole) in dry tetrahydrafuran (THF) (freshly distilled from lithium aluminum hydride) (LAH), 600 ml) was stirred at RT for 1.0 hr. A solution of 2 (35.0 g, 0.191 mole) in dry THF (500 ml) was added all at once. The resulting mixture was stirred at RT for 18 hrs. It was then cooled (ice bath) and ice-$H_2O$ (700 ml) added dropwise (much effervescence at first). Cold 6N HCl (110 ml) was then added (to a pH of 1.5) and the resulting clear solution stirred at RT for 1.0 hr. Evaporation, azeotroping with MeOH (4×500 ml), then with pyridine (2×500 ml) gave a mixture of white solid and pale yellow syrup. Pyridine (250 ml) was added, and the insoluble inorganics filtered off. Acetic anhydride (250 ml) was added to the pyridine filtrate and stirring continued at RT for 18 hrs. After evaporation, MeOH (250 ml) was added to the residual syrup and the resulting solution refluxed for 10 min. After evaporation of the MeOH, the residue was stirred with $CH_2Cl_2$ (500 ml)-$H_2O$ (250 ml) while sufficient solid $NaHCO_3$ was added to make the aqueous layer basic. The layers were separated and the aqueous layer was extracted with additional $CH_2Cl_2$ (2×250 ml). The combined $CH_2Cl_2$ layers were dried ($CaSO_4$) and evaporated. The residue was azeotroped with toluene (3×250 ml), leaving a yellow oil (39.1 g); pmr almost identical to that of an analytical sample. Distillation gave a colorless syrup (36.7 g, 98%), bp 132°–134° (0.04 mm), which solidified on standing to white crystals, mp 62°-63°. Sublimation of such a sample (60°, 0.1 mm) gave an analytical sample of 3 as white crystals: mp 62°-63°.

(±)-4α-Acetamido-2α, 3α-epoxycyclopentane-1α-methyl Acetate (4). A solution of 3 (36.7 g, 0.186 mole) and m-chloroperbenzoic acid (37.8 g, 85%, 0.186 mole) in $CCl_4$ (700 ml) was refluxed for 2.0 hrs. The solution was concentrated to 200 ml and $CH_2Cl_2$ (500 ml) added. This solution was extracted with sat'd $NaHCO_3$ (150 ml), dried ($CaSO_4$), and evaporated, leaving 4 as a yellow oil (40.8 g) which solidified on standing.

(±)-4α-Acetamido-2β, 3α-diacetoxy-1α-cyclopentanemethyl Acetate (5) and (±)-4α-Acetamido-2α, 3β-diacetoxy-1α-cyclopentanemethyl Acetate (6). A solution of crude 4 (7.42 g, 34.8 mmoles) in 2% $H_2SO_4$ (450 ml) was warmed (steam bath) for 1.0 hr. A small amount of gummy solid was filtered off (mostly m-chlorobenzoic acid contaminating 4). The pH of the cooled filtrate was adjusted to 7 (indicator paper) with 6 N NaOH. The $H_2O$ was evaporated and the residue dissolved in pyridine (2×200 ml) and evaporated. The residual syrup was dissolved in $Ac_2O$ (100 ml)-pyridine (200 ml) and stirred at RT overnight. After evaporation, the residue was dissolved in $CH_2Cl_2$ (250 ml), extracted with sat'd ($NaHCO_3$ (25 ml), and dried ($CaSO_4$). Evaporation, followed azeotroping off pyridine with toluene, left brown syrup (9.61 g). Crystallization from EtOAc gave 5 as white prisms (5.77 g, 53%), mp 137.5°–138.5°.

The mother liquors from crystallization of 5 contained an approximately 1:1 mixture of 5 and 6 (from NH resonances in pmr spectrum). Although some slight separation appeared on the (5% MeOH-$CHCl_3$, silica gel), column chromatography of the mother liquor contents on silica gel (250 g) with elution by 1% MeOH—$CHCl_3$ gave only a slight enrichment of the early fractions in the minor isomer (about 60:40 by pmr). The mixture of 5 and 6 (3.30 g, 10.5 moles) was dissolved in 2 N HCl (100 ml) and maintained at 70° (oil bath) for 1.0 hr. The solution was evaporated to dryness. The residue was dissolved in $H_2O$ and the solution stirred briefly with IRA-400($OH^-$) resin (30 ml). The solution (presumed to be 7+6a) was passed slowly through a column of IRA-120($^+$) resin (60 ml). Elution of the column with $H_2O$ and azeotroping with abs. EtOH produced 6a as a colorless syrup (1.13 g, 5.97 mmoles, 17% from 4). The syrup was reacetylated in $Ac_2O$-pyridine (as above), giving 6 as a colorless syrup (1.58 g, 14% from 4).

(±)-4α-Amino-2β, 3α-dihydroxy-1α-cyclopentanemethanol (7). A solution of 5 (3.37 g, 10.7 mmoles) in 2 HCl (100 ml) was maintained at 70° (oil bath) for 1.0 hr. The solution was evaporated to dryness and the residue dissolved in MeOH (100 ml) and stirred briefly with IRA-400($OH^-$) resin (25 ml). Evaporation left 7 as a viscous syrup which could not be solidified and turned yellow on standing. Since 7 appeared to carbonate on exposure to air, it was used immediately.

5-amino-4N-[2α, 3β-dihydroxy-4α-(hydroxymethyl)-cyclopent-1α-yl]amino-6-chloropyridimide (8). A solution of 7 (syrup from hydrolysis of 10.7 mmoles of 5), 5-amino-4,6-dichloropyrimidine (3.51 g, 21.4 mmoles), and triethylamine (7.5 ml, 53.5 mmoles) in 1-BuOH (50 ml) was refluxed under $N_2$ for 24 hrs. The solution was evaporated to dryness and the residue partitioned between $H_2O$ (80 ml) and $CHCl_3$ (40 ml). The aqueous layer was separated and extracted with additional $CHCl_3$ (3×10 ml). The combined $CHCl_3$ layers showed only 5-amino-4,6-dichloropyrimidine on tlc. The aqueous layer was stirred briefly with IRA-400(OH⁻) resin (18 ml). The H₂O was then evaporated and the residue dried by azeotroping with abs. EtOH, giving chromatographically homogeneous 8 as a pale yellow glass (3.4 g, contains EtOH). Such a sample was sufficiently pure for use in the following reactions. Two recrystallizations of such a sample from abs. EtOH gave 8 as an off-white powder, 72% from 5: mp 184°-186°.

EXAMPLE 2

The purine nucleoside analog (±)-6-Chloro-9-[2α, 3β-dihydroxy-4α-(hydroxymethyl)cyclopent-1α-yl]purine (9) was prepared as follows:

A solution of crude 8 (ca. 4.8 mmoles) in diethoxymethyl acetate (20 ml) was stirred at RT overnight and then at 100° (oil bath) for 1.0 hr. The solution was evaporated and then azeotroped with abs. EtOH and dried at 0.05 mm for 2 days. The residual brown syrup (3.4 g) still smelled like diethoxymethyl acetate; tlc shows several spots at $R_f$ greater than that of 8 or 9. The syrup was stirred vigorously with 0.5 N HCl (120 ml) at RT for 30 min. The resulting solution was adjusted to pH 7.8 (meter) by addition of IRA-400 (OH⁻) resin evaporation left while solid (0.98 g, 72%), which tlc showed to be chromatographically homogeneous 9. An analytical sample of 9 was prepared by two recrystallization of such a sample from abs. EtOH, giving white clusters of needles: mp 210°-212° dec.

EXAMPLE 3

The amino substituted derivative (10a) of the -6-substituted purine 10 was prepared from the intermediate 8 as follows:

(±)-9-[α-(2α, 3β-Dihydroxy-4α(hydroxymethyl)cyclopentyl]adenine (C-ara-A) (10a). A solution of crude 8 (ca. 4.1 mmoles) in diethoxymethyl acetate (25 ml) was stirred at RT overnight and then at 100° (oil bath) for 1.0 hr. Alternatively, triethyl orthoformate has been used to close the ring. The solution was evaporated to dryness and the residue shaken with NH₃ (1., 50 ml) in a stainless steel bomb at RT overnight. The NH₃ was allowed to evaporate and the residue dissolved in 1 N HCl (100 ml) and stirred at 60° (oil bath) for 45 min. The solution was evaporated to dryness, the residue dissolved in MeOH and passed through a column of IRA-400(OH⁻) resin (20 ml). The MeOH eluent (250 ml) was evaporated, the tan solid residue (870 mg) was triturated with abs (EtOH, giving 10a as white powder (824 mg, 76%), mp 253°-255° dec.

EXAMPLE 4

The hydroxyl substituted derivative (10b) of the -6-substituted purine 10 was prepared as follows:

(±)-9-[2α, 3β-Dihydroxy-4α-(hydroxymethyl)cyclopent-1α-yl]hypoxanthine (10b). A sample of 8 (2.0 mmoles) which had been treated with diethoxymethyl acetate as described in Example 2 in the preparation of 9 was then refluxed in 1N HCl (25 ml) for 3.5 hrs. The solution was evaporated to dryness and the residue dissolved in H₂O (25 ml). The pH was adjusted to 5-6 by addition of IRA-400 (OH⁻) resin in small portions. Evaporation, followed by azeotroping with abs. EtOH, left chromatographically homogeneous 10b as a white powder (257 mg), mp 220°-222° dec. Crystallization from MeOH gave white granules (247 mg, 46%): mp 221.5°-223.5° dec.

EXAMPLE 5

The mercapto substituted derivative (10c) of the -6-substituted purine 10 was prepared as follows:

(±)-9-[2α, 3β-Dihydroxy-4α-(hydroxymethyl)cyclopent-1α-yl]-9H-purine-6-(1H)-thione (10c). A solution of 9 (310 mg, 1.09 mmoles) and thiourea (142 mg, 1.86 mmoles) in 1-propanol (8 ml) was refluxed for 45 min., at which time white solid had precipitated. The mixture was cooled and the solid filtered off and washed with 1-propanol (2×2 ml), giving 12 as white powder (237 mg, 77%), same melting characteristics and tlc as an analytical sample. Crystallization from H₂O gave an analytical sample of 12 as white granules (185 mg): mp dependent of rate of heating, starts to dec. at ca. 270°, black fluid by ca. 280°.

EXAMPLE 6

The methylmercapto substituted derivative (10d) of the -6-substituted purine 10 was prepared as follows:

(±)-9-[2α, 3β-Dihydroxy-4α(hydroxymethyl)cyclopent-1α-yl]-6-(methylthio)purine (10d). A mixture of crude 10c (174 mg, 0.616 mmole), methyl iodide (0.25 ml), 1.0 N NaOH (0.62 ml), and H₂O (2.0 ml) was stirred at RT for 4.0 hrs. The resulting solution was evaporated to dryness and the residue chromatographed on a column of silica gel G (Brinkmann, 20 g, packed in CHCl₃). Elution with 5% MeOH—CHCl₃ and combination of the UV-absorbing fractions gave 10d as white powder (45 mg, 25%), chromatographically homogeneous. Resolidification of such a sample from abs. EtOH gave an analytical sample as white flakes: mp 232°:234°.

EXAMPLE 7

The amino substituted derivative (12a) of the -7-substituted pyrimidine 12 was prepared as follows:

(±)-7-Amino-3-[α-(2α, 3β-dihydroxy-4-(hydroxymethyl)cyclopentyl]-v-Triazolo[4,5d]pyrimidine (12a). To a cooled (ice bath) solution of 8 (526 mg, 1.91 mmoles) in 0.5 N HCl (10 ml) was added NaNO₂ (159 mg, 2.30 mequiv). After 5 min., the ice bath was removed and the solution was stirred at RT for 1.0 hr. Solid NaHCO₃ (420 mg) was added and the solution was evaporated to dryness. The residue was shaken with NH₃ (20 ml) in a steel bomb at RT for 20 hrs. After evaporation of the NH₃, the residue was solidified from H₂O, giving white solid (294 mg, 58%), mp 258°-262° dec.

EXAMPLE 8

The cytotoxicity of C-ara-A was evaluated by growing P-388 mouse lymphoid leukemia cells in the presence of either (C-ara-A) or ara-A using the method described by Almquist et al., *J. Med. Chem.*, 16, 1396 (1973). Both ara-A and C-ara-A exhibited LD₅₀ concentrations of $1 \times 10^{-5}$ M. In contrast to ara-A, the carbocyclcic analog C-ara-A is completely resistant to deamination by adenosine deaminase. Thus, under conditions in which ara-A is completely deaminated (1 μmole/min/unit of enzyme) by calf intestinal adenosine deaminase (type III, Sigma) no detectable deamination of C-ara-A was observed. In addition, C-ara-A did not inhibit the enzymatic deamination of either ara-A or adenosine.

EXAMPLE 9

C-ara-A was examined for in vitro antiviral activity against two representative DNA-containing animal viruses by the quantitative determination of its ability to inhibit virus-induced cytopathogenic effects (cpe) in infected cultures. The viruses employed in these assays were herpes simplex virus (HSV) type 1 (strain HF) and vaccinia virus (VV) (Strain Lederle Chorioallantoic). Both viruses were propagated and assayed for infectivity in continuous-passage human epidermoid carcinoma of the larynx (HEp-2) cells. A virus rating (VR) was calculated for the activity of C-ara-A against each virus by the use of a modification of the method of Ehrlich et al., *Ann. N.Y. Acad. Sci.*, 130, 5 (1965) previously described by Sidwell et al., *Proc. Soc. Exp. Biol. Med.*, 131, 1226 (1969), except that triplicate cultures rather than duplicate cultures were employed for each assay. The results are shown in Table 1:

TABLE I

In Vitro Antiviral Activity of Carbocyclic Ara-A

| Challenge Virus | Virus Rating (VR)[a] | MED$_{50}$[b] (μg/ml) |
|---|---|---|
| Herpes simplex virus, type 1 | 2.2 | 9.0 |
|  | 3.5 | 2.8 |
| Vaccinia virus | 1.5 | 9.0 |
|  | 1.7 | 9.0 |

[a]Virus rating (VR): a weighted measurement of antiviral activity, based on the in vitro inhibition of virus-induced cytopathogenic effects (cpe) and the cytotoxicity exhibited by the drug, determined by a modification of the method of Ehrlich et al. (supra). A VR ≧ 1.0 indicates definite (+) antiviral activity; a VR of 0.5–0.9 indicates marginal to moderate (±) antiviral activity; and a VR < 0.5 indicates no (−) apparent antiviral activity
[b]Minimum effective dose, 50% (MED$_{50}$): the minimum drug dose required for 50% inhibition of virus-induced cpe.

As can be seen, the carbocyclic analog of ara-A demonstrated highly significant antiviral activity against HSV and VV with VR's ranging from 1.5 to 3.5. The approximate MED$_{50}$ for C-ara-A appears to be about 9 g/ml.

Compounds 3 and 4 may also be prepared as benzoates or p-nitrobenzoate.

EXAMPLE 10

A chemotherapy experiment with carbocyclic ara-A against lethal HSV-1 infections in mice was conducted by an independent research laboratory. The data are contained in the two following summary tables: Table 2 shows the actual death patterns for treated and control mice and also gives the average body weights of the animals on days 0, 7, 14 and 21. Table 3 summarizes the mortality and mean survival time data in a format suitable for publication.

It can be seen that 95 per cent of the virus-inoculated control mice died, with a mean survival time of 8.4 days for the dying animals. The positive control drug (ara-A) exhibited significant in vivo activity in this model system by reducing the mortality down to 0 to 10 percent when administered at non-toxic dose levels of 125 to 250 mg/kg/day on the qd 1-7 schedule. Likewise, the carbocyclic analog of ara-A (C-ara-A) was also found to be highly effective in the treatment of these HSV-1 infections in mice, reducing the mortality down to 0 to 10 percent when administered at the non-toxic dose levels of 112.5 to 450 mg/kg/day on the same schedule. C-ara-A at 900 mg/kg/day was apparently not lethally toxic for uninfected animals, but proved to be quite toxic for the HSV-infected mice. The mean survival time of dying animals in this latter group was observed to be significantly reduced to 4.3 days. The increase in mean survival time of the one dying animal which was treated with C-ara-A at 450 mg/kg/day was not statistically significant. These data indicate that carbocyclic ara-A is essentially as active as ara-A against HSV-1 in vivo.

TABLE 2

The Effect of Carbocyclic Arabinosyladenine (C—Ara—A) Treatment on Herpes Simplex Virus, Type 1, Infections in Mice

| Host: | Random-bred Swiss mice, female, from Charles River Breeding Laboratories, Inc. | Drug Treatment: | C—Ara—A was suspended in 0.9% NaCl solution contaning 0.3% hydroxypropylcellulose (HPC) at four different concentrations so that a single daily dose volume of 0.01 ml/gm of body weight equaled 900, 450, 225, and 112.5 mg/kg/day. 9-β-D-arabinofuranosyladenine (NSC 404241; Ara—A) was suspended in the same manner so that a single daily dose volume of 0.01 ml/gm of body weight equaled 250 and 125 mg/kg/day. The drugs were administered once daily for 7 days beginning 4 hours after virus inoculation. |
|---|---|---|---|
| Virus: | Herpes simplex virus, type 1, strain HS-123. Equal volumes of 10% mouse brain suspensions from the 8th and 9th intracerebral (i.c.) mouse passages were pooled and diluted 1:3 in phosphate-buffered saline (PBS). The mice were infected by inoculating each mouse intraperitoneally (i.p.) with 0.3 ml of the 1:3 dilution. | | |
| Period of Observation: | 21 days. | | |

| Drug Dose mg/ kg/day | Animal Group | Death Pattern No. of Days Post-Virus Inoculation: 3 | 4 | 5 | 6 | 7 | 8 | 9 | 10 | 11 | 12 | 13 | 14 | 15-21 | Mortality: No. Dead/ Total No. of Mice | (%) | Avg. Body Wt. gm on Day: 0 | 7 | 14 | 21 |
|---|---|---|---|---|---|---|---|---|---|---|---|---|---|---|---|---|---|---|---|---|
| 0 | Virus controls, untreated | | | | 4 | 4 | 4 | 1 | 3 | 1 | 1 | | 1 | | 19/20 | 95 | 19.8 | 21.5 | 25 | 26.5 |
| 900 | C—Ara—A + virus | 2 | | | | 1 | | | | | | | | | 3/10 | 30 | 19.8 | 18.1 | 20.6 | 22.6 |
| | C—Ara—A toxicity controls | | | | | | | | | | | | | | 0/5 | 0 | 21.8 | 22.5 | 25.3 | 28 |
| 450 | C—Ara—A + virus | | | | | | | | 1 | | | | | | 1/10 | 10 | 19.7 | 19.3 | 23.3 | 23.8* |
| | C—Ara—A toxicity controls | | | | | | | | | | | | | | 0/5 | 0 | 21.6 | 22.6 | 25.9 | 28.3 |
| 225 | C—Ara—A + virus | | | | | | | | | | | | | | 0/10 | 0 | 19.6 | 21.8 | 24.1 | 25.6 |
| | C—Ara—A toxicity controls | | | | | | | | | | | | | | 0/5 | 0 | 21.8 | 24.4 | 26.8 | 29.3 |
| 112.5 | C—Ara—A + virus | | | | | 1 | | | | | | | | | 1/10 | 10 | 19.9 | 22.4 | 24 | 26.9 |
| | C—Ara—A toxicity controls | | | | | | | | | | | | | | 0/5 | 0 | 21.8 | 24.5 | 26.5 | 28.5 |
| 250 | Ara—A + virus | | | | | 1 | | | | | | | | | 1/10 | 10 | 19.9 | 20.3 | 23.1 | 25.9 |
| | Ara—A toxicity controls | | | | | | | | | | | | | | 0/10 | 0 | 21.7 | 25.1 | 26.6 | 29.1 |
| 125 | Ara—A + virus | | | | | | | | | | | | | | 0/10 | 0 | 20 | 23.4 | 25.9 | 28.2 |

TABLE 2-continued
The Effect of Carbocyclic Arabinosyladenine (C—Ara—A) Treatment on Herpes Simplex Virus, Type 1, Infections in Mice

|   |                          |      |   |      |      |      |      |
|---|--------------------------|------|---|------|------|------|------|
|   | Ara—A toxicity controls  | 0/10 | 0 | 21.7 | 25.4 | 27.3 | 29.5 |
| 0 | HPC, sham-injected i.p. qd 1-7 | 0/10 | 0 | 23.5 | 26.8 | 29.7 | 31.7 |
| 0 | PBS, sham-injected i.p. 1X | 0/10 | 0 | 22   | 27.7 | 29.4 | 31.7 |
| 0 | Normal, untreated animals | 0/15 | 0 | 22.5 | 27.1 | 29.0 | 31.2 |

*Note: One animal, moribund on day 21, weighed 11.5 gm. This animal had been sick 4-5 days.

TABLE 3
Effect of Treatment with Ara—A and with the Carbocyclic Analog of Ara—A (C—Ara—A) on Mortality of Random-bred Swiss Mice Inoculated i.p. with *Herpesvirus hominis* type 1

| Drug | Drug Dose (mg/kg/day)[1] | Virus-infected Animals | | | Uninfected Animals | |
|---|---|---|---|---|---|---|
| | | Mortality (No. dead/total) | % | Mean Survival Time (days)[2] | Mortality (No. dead/total) | % |
| None | — | 19/20 | 95 | 8.4 | 0/35 | 0 |
| Ara—A[3] | 250 | 1/10 | 10*[4] | 7.0 | 0/10 | 0 |
| " | 125 | 0/10 | 0* | — | 0/10 | 0 |
| C—Ara—A[3] | 900 | 3/10 | 30** | 4.3+ | 0/5 | 0 |
| " | 450 | 1/10 | 10* | 11.0++ | 0/5 | 0 |
| " | 225 | 0/10 | 0* | — | 0/5 | 0 |
| " | 112.5 | 1/10 | 10* | 7.0 | 0/5 | 0 |

[1] Drugs were administered i.p. once daily for seven days beginning 4 hours after virus inoculation.
[2] Only animals dying on or before day 21 after virus inoculation were considered.
[3] Ara—A = 9-β-D-Arabinofuranosyladenine. C—Ara—A = Carbocyclic analog of 9-β-D-Arabinofuranosyladenine.
[4] Probability that the observed increase in survivor number ($\chi^2$-test) or the observed increase or reduction in mean survival time (t-test) was due to chance. *p < <0.0005; **p <0.001; +p <0.005; ++p >0.10. A p-value of <0.05 was considered to indicate a signficiant difference; a p-value of <0.001 was considered to indicate a conclusive difference.

Acid salts of C-ara-A are prepared as follows:

EXAMPLE 11

(±)-9-[2α, 3β-dihydroxy-4α-(hydroxymethyl)cyclopent-1α-yl]adenine hydrochloride. To 283 mg (1 mmole) of 10a was added 10 ml of 0.1N hydrochloric acid. The solution was warmed to 602° for five minutes and then evaporated in vacuo to a white solid. The solid was triturated with absolute ethanol, (10 ml) at 0°-5°. The analytical product was obtained by filtration of the triturate and gave a crystalline solid: 250 mg.

EXAMPLE 12

The crystalline sulphate salt was obtained when 10 ml of 0.1N sulfuric acid was added to 283 mg of 10a and the reaction mixture was treated as in Example 11 above.

EXAMPLE 13

The monophosphate ester of C-ara-A (10a):

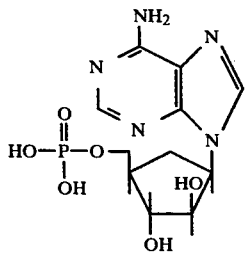

13a was prepared as follows:

(±)-9-[2α, 3β-dihydroxy-4α-(hydroxymethyl)cyclopent-1α-yl]adenine 4-dihydrogen phosphate (13a). A solution of trimethyl phosphate (6 ml), 10a (567 mg) and phosphoryl chloride (0.37 ml) was stirred at −10° for 3 hours and the clear solution was then poured into water (175 ml) and the solution was stirred at rt for 1 hour, neutralized with ammonium hydroxide and passed through a column of Amberlite (H+) resin (20 g). The column was washed with water, then 1N ammonium hydroxide (500 ml). The basic eluent was evaporated to dryness and the residue was dissolved in water. To this solution was added 6N hydrochloric acid (0.35 ml) and ethanol (5 ml). The solution was cooled to −20° and allowed to refrigerate overnight. The pure product was removed by filtration and gave a white solid: yield, 368 mg; mp 230°-232°.

EXAMPLE 14

The monoesters of C-ara-A (10a):

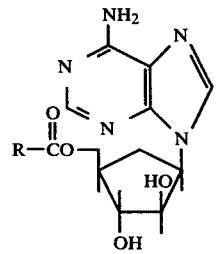

14a wherein R is H, $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, $C_{11}H_{23}$, $C_{12}H_{25}$, $C_{13}H_{27}$, $C_{14}H_{29}$, $C_{15}H_{31}$ or $C_{16}H_{33}$ were prepared by condensation of the corresponding acid chloride with 10a according to the general procedure exemplified by the preparation of the valerate ester (R=$C_4H_9$):

(±)-9-[2α, 3β-dihydroxy-4α-(hydroxymethyl)cyclopent-1α-yl]adenine 4-valerate. The hydrochloride salt of 10a (73 mg) was suspended in 3 ml of dimethylformamide. Valeryl chloride (35 mg) in 1 ml of dimethylformamide was added dropwise to the suspension, and the reaction mixture was stirred at room temperature overnight. After removal of the solvent, the residue was dissolved in water and the aqueous solution was washed with chloroform to remove excess valeryl chloride. The aqueous solution was neutralized with sodium bicarbonate and extracted with ethyl acetate. The organic layer was dried with anhydrous sodium sulfate and evaporated to yield a solid product (30 mg). The solid was purified on a prep-tlc (silica gel) plate developed with 20 percent methanol in methylene chloride. The pure valerate was extracted from the silica gel with the developing solvent and yielded a white powder; mp 151°–153°, mass spectra m/e 349 (M+.).

EXAMPLE 15

The formate ester (R=H) was prepared by dissolving 10a in anhydrous formic acid and allowing the resulting solution to stand for 4 days at 5°. Isolation of the ester was as in Example 14 above.

It is apparent that many modifications and variations of this invention as hereinbefore set forth may be made without departing from the spirit and scope thereof. The specific embodiments described are given by way of example only and the invention is limited only by the terms of the appended claims.

The embodiments of the invention in which an exclusive property or privilege is claimed are defined as follows:

1. A method of preparation of the purine nucleoside analog having the formula:

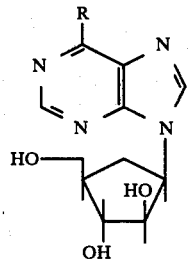

wherein R is selected from the group of substituent groups consisting of amino, hydroxyl, mercapto, methylmercapto and substituted amino NR'R" wherein R' and R" may be the same or different and are hydrogen, methyl, ethyl, propyl or phenyl, which method comprises:

(A) preparing the intermediate

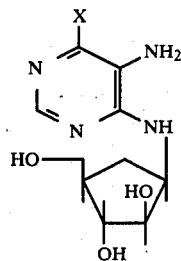

wherein X is halogen, by
(1) hydrolysing 2-azabicyclo[2.2.1]hept-5-en-3-one under acid conditions.
(2) esterifying the carboxyl function of the resulting cis-4-aminocyclo-pent-2-ene carboxylic acid salt,
(3) acetylating the amino group of the resulting ester,
(4) reducing and acetylating said ester,
(5) epoxidizing the resulting acetate,
(6) hydrolysing and acetylating the resulting epoxide,
(7) forming an amine from the resulting (±)-4α-acetamido-2β, 3α-diacetoxy-1α-cyclopentanemethyl acetate, and
(8) condensing said amine with 5-amino-4,6-dihalopyrimidine to produce said intermediate;
(B) closing the ring of said intermediate by reaction with a ring closing agent selected from the class consisting of diethoxymethyl acetate and triethyl orthoformate, and
(C) replacing the halogen with a substituent from the group consisting of amino, hydroxyl, mercapto, methylmercapto and substituted amino.

2. A method according to claim 1 further characterized in that R is NH₂ and said halogen is replaced by reaction with ammonia.

3. A method according to claim 1 further characterized in that R is OH and said halogen is replaced by refluxing in aqueous acid.

4. A method according to claim 1 further characterized in that R is SH and said halogen is replaced by reaction with thiourea.

5. A method according to claim 1 further characterized in that R is SCH₃, said halogen is replaced by a mercapto group by reaction with thiourea and said mercapto is methylated by reaction with methyl iodide.

* * * * *

UNITED STATES PATENT AND TRADEMARK OFFICE
CERTIFICATE OF CORRECTION

PATENT NO. : 4,268,672
DATED : May 19, 1981
INVENTOR(S) : Robert Vince

It is certified that error appears in the above-identified patent and that said Letters Patent are hereby corrected as shown below:

Column 4, line 37, "moles" should be --mmoles--.

Column 4, line 51, after "2" --N-- is omitted.

Column 9, line 37, "602°" should be --60°--.

Signed and Sealed this

Twenty-fifth Day of August 1981

[SEAL]

Attest:

Attesting Officer

GERALD J. MOSSINGHOFF

Commissioner of Patents and Trademarks